(12) United States Patent
Tatum

(10) Patent No.: US 12,702,781 B2
(45) Date of Patent: Aug. 11, 2026

(54) MEDICINAL DIFFUSER

(71) Applicant: Dan Tatum, Brookhaven, PA (US)

(72) Inventor: Dan Tatum, Brookhaven, PA (US)

( * ) Notice: Subject to any disclaimer, the term of this patent is extended or adjusted under 35 U.S.C. 154(b) by 815 days.

(21) Appl. No.: 17/896,552

(22) Filed: Aug. 26, 2022

(65) Prior Publication Data

US 2024/0066248 A1 Feb. 29, 2024

(51) Int. Cl.
*A61M 16/06* (2006.01)
*A61M 16/08* (2006.01)
*A61M 16/14* (2006.01)

(52) U.S. Cl.
CPC .... *A61M 16/0666* (2013.01); *A61M 16/0816* (2013.01); *A61M 16/14* (2013.01)

(58) Field of Classification Search
CPC .................................................. A61M 16/0666
USPC ...................................................... 128/203.22
See application file for complete search history.

(56) References Cited

U.S. PATENT DOCUMENTS 4,054,133 A * 10/1977 Myers ............... A61M 16/0677 128/207.18
4,753,233 A * 6/1988 Grimes ............. A61M 16/0666 128/207.18
4,782,832 A * 11/1988 Trimble ............ A61M 16/0633 128/207.18
4,919,128 A * 4/1990 Kopala ............. A61M 16/0666 128/207.18
6,089,229 A * 7/2000 Bathe .................... A61M 16/12 128/204.21
6,561,188 B1 * 5/2003 Ellis ........................ A62B 23/06 128/207.18
7,727,194 B2 * 6/2010 Nalagatla .......... A61M 16/0808 604/122
7,762,253 B2 * 7/2010 Acker ............... A61M 16/0858 128/207.18
8,333,199 B2 * 12/2012 Landis ............. A61M 16/0666 128/207.18
8,770,199 B2 * 7/2014 Flanagan ............ A61M 16/009 128/207.18
9,027,562 B1 * 5/2015 Heyman ........... A61M 16/0672 128/207.18
9,919,124 B2 * 3/2018 Ahmad ............. A61M 16/0833
10,328,229 B2 * 6/2019 Alizoti ................ A61M 15/009
D884,154 S * 5/2020 McNally ........... A61M 16/0672 D24/110.4
10,792,449 B2 * 10/2020 Brambilla ......... A61M 16/0096
11,154,672 B2 * 10/2021 Allum ................. A61M 16/024

(Continued)

FOREIGN PATENT DOCUMENTS

EP 1007122 B1 7/2005

OTHER PUBLICATIONS

VBM Product Catalogue, Accessories for Anesthesia & Intensive Care, (https://raydan-company.com/wp-content/uploads/catalogs/anaesthesia-and-intensive-care.pdf), Feb. 2019.*

*Primary Examiner* — Clinton T Ostrup
(74) *Attorney, Agent, or Firm* — Barley Snyder

(57) ABSTRACT

A medicinal diffuser system for patients is provided and includes a nasal cannula, a flow stream vessel and a mount assembly. The medicinal diffuser system is mountable over a patient's head and permits a steady flow of air while administering a medicinal agent. The medicinal diffuser permits a steady flow of air to flow into the patient's nasal cavity while administering a medicinal agent.

18 Claims, 8 Drawing Sheets

(56) References Cited

U.S. PATENT DOCUMENTS 11,364,358 B2 * 6/2022 Cortez, Jr. ............. A61M 11/00
11,878,115 B2 * 1/2024 Leonard ............ A61M 16/0666
12,005,190 B2 * 6/2024 Urie .................... A61M 16/085
2002/0017300 A1 * 2/2002 Hickle ................. A61B 5/0836 128/204.22
2002/0104531 A1 8/2002 Malone
2002/0112730 A1 * 8/2002 Dutkiewicz ....... A61M 16/0666 128/207.18
2003/0168067 A1 * 9/2003 Dougill ............. A61M 16/0666 128/207.18
2007/0107737 A1 * 5/2007 Landis .............. A61M 16/0666 128/207.18
2008/0121230 A1 * 5/2008 Cortez .............. A61M 16/0688 128/207.18
2008/0190435 A1 8/2008 Hansen
2008/0223375 A1 * 9/2008 Cortez .............. A61M 16/0688 128/207.18
2010/0043801 A1 * 2/2010 Halling ............. A61M 16/0666 128/207.18
2011/0247616 A1 * 10/2011 Von Hollen ...... A61M 15/0026 128/203.12
2012/0318274 A1 * 12/2012 Ho .................... A61M 16/0683 128/207.18
2013/0306060 A1 * 11/2013 Cota ..................... A61M 39/08 128/200.14
2014/0150789 A1 * 6/2014 Flanagan ............ A61M 16/204 128/203.22
2014/0158121 A1 * 6/2014 Flanagan .......... A61M 16/1005 128/203.12
2014/0158127 A1 * 6/2014 Boucher ................ A61M 11/00 128/203.22
2015/0068530 A1 * 3/2015 Apolito ............ A61M 16/0683 128/207.18
2015/0083123 A1 * 3/2015 Tero .................. A61M 16/0003 128/205.25
2015/0165151 A1 * 6/2015 Payton .............. A61M 16/0688 128/205.25
2015/0217074 A1 * 8/2015 Wells .................... A61M 16/06 128/207.18
2016/0038008 A1 * 2/2016 Molnar .............. A61B 1/00137 600/110
2019/0125256 A1 * 5/2019 Hays ........................ A61B 5/11
2019/0366022 A1 * 12/2019 Leonard ............... A61M 11/042
2021/0093809 A1 * 4/2021 Leonard ............... A61M 11/005
2021/0128849 A1 * 5/2021 McNally ............... A61M 15/08
2022/0379067 A1 * 12/2022 Varga ................ A61M 16/0866
2025/0312549 A1 * 10/2025 Salvino ............ A61M 16/0672

* cited by examiner 1
20

120
70
172
174
90
A
140
142
150
80

90
170
A
C
B
80
150
100

150
14
104
C
B
100
14

42
46
36
90
80

32

42
48

32
42
38
32

94
46
36
44
42
34
84
90
94
84
80
104
160
176
172
150
174
140

MEDICINAL DIFFUSER

FIELD OF INVENTION

The invention relates to a medicinal diffuser and, more particularly to a medicinal diffuser that allows continuous air flow while administering a medicinal agent.

BACKGROUND

Medical devices that enhance the care of a patient have always been an interest in the medical field. In particular, nasal cannulas are well known in the art. While it is customary to deliver medicinal agents to a patient, it is also difficult, no matter the age of the patient. For example, a common method of inducing anesthesia is through the inhalation of medicinal agents through a face mask. However, the delivery of medicinal agents through a face mask to a patient whether they are a neonate, pediatric or adult is often difficult. There are numerous factors that could contribute to this difficulty such as, a short attention span, trauma, fear/nervousness, and/or an inability to comprehend the importance of inhaling medicinal agents. The lack of cooperation exhibited by many patients during the course of attempting to administer medicinal agents can result in increased anxiety on the part of the patient, the patient's guardians, and the medical worker.

Therefore, there is a need for a device that would allow for continuous air flow while administering medication to a patient. Moreover, for a device that would aid in reducing the anxiety and aid in inhaling the necessary medication.

SUMMARY

The claimed invention overcomes the problems of the known prior art and provides an improved medicinal diffuser for a patient, while continuously supplying a steady flow of oxygen.

The medicinal diffuser system comprises a nasal cannula having an air flow nasal prong with a set of nasal receivers, and a medicinal flow nasal prong having a set of medicinal distributors positioned integral to an outer wall of each nasal receiver. The medicinal diffuser system further comprises a flow stream vessel having a set of air flow tubes independently connected to air flow nasal prong, and a medicinal flow tube independently connected to the medicinal flow nasal prong. The medicinal diffuser system further comprises a mount assembly having an air passage device in communication with the set of airflow tubes and releasably connectable with an air supply, and a luer lock connector connected to the medicinal flow tube and releasably connectable to a medicinal supply to allow for a steady flow of medicine to be released independent of the air supply.

BRIEF DESCRIPTION OF DRAWINGS

The invention will now be described by way of example with reference to the accompanying figures, of which.

DETAILED DESCRIPTION OF THE EMBODIMENT(S)

Figures 1, 2:
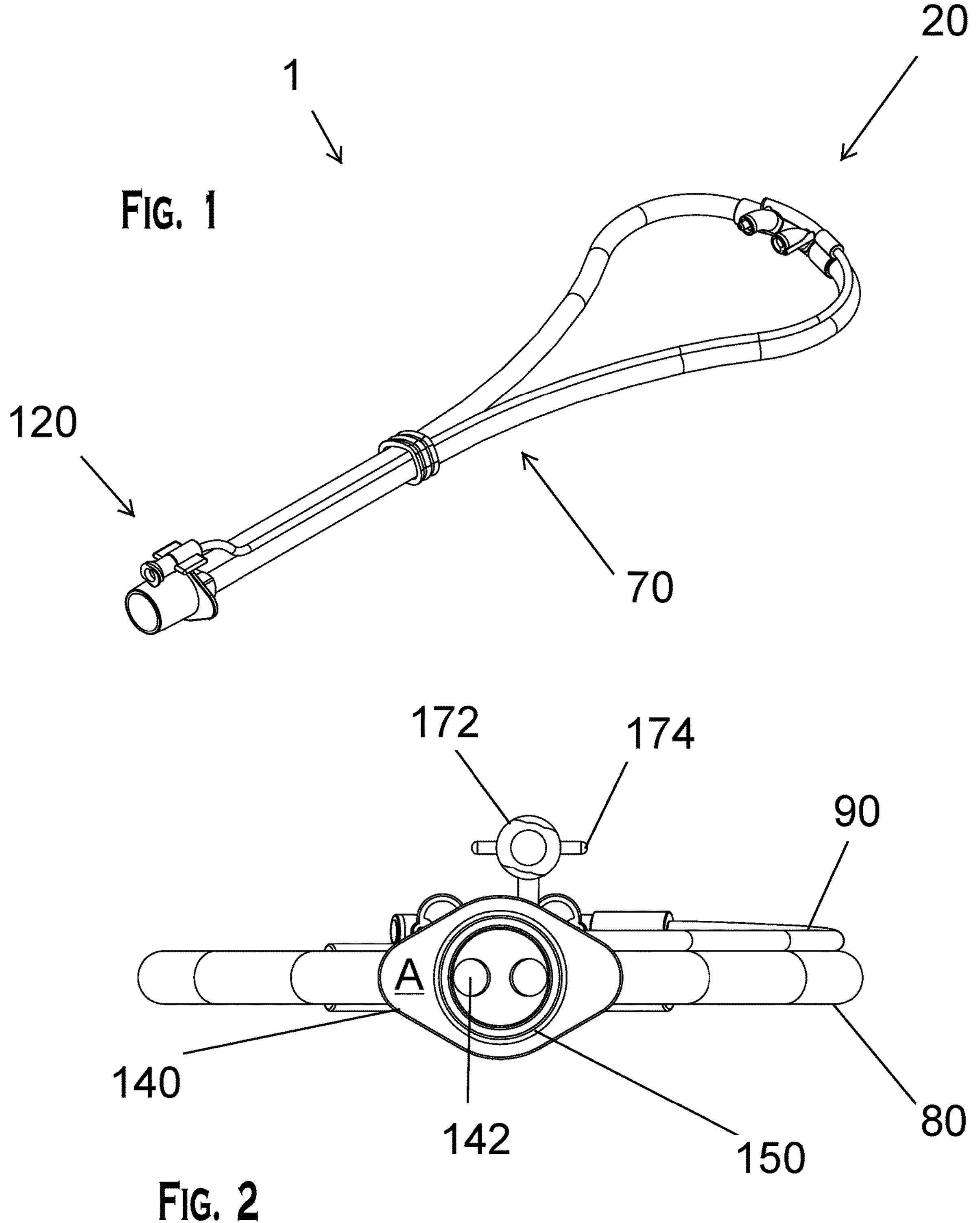
FIG. 1 is a rear, right, top perspective view of a medicinal diffuser.
FIG. 2 is a rear perspective view of the invention of FIG. 1.

Exemplary embodiments of the invention will be described hereinafter in detail with reference to the attached drawings, wherein like reference numerals refer to like elements.

The invention may, however, be embodied in many different forms and should not be construed as being limited to the particular embodiments set forth herein; rather, these embodiments are provided so that the present disclosure will be thorough and complete, and will fully convey the concept of the disclosure to those skilled in the art.

The FIGS. 1-16 establish the components and overall structure of a medicinal diffuser system 1, according to the exemplary embodiments of the invention.

In the exemplary embodiment shown in FIG. 1, the medicinal diffuser system 1 is generally constructed in accordance with the following major components: a nasal cannula 20, a flow stream vessel 70, and a mount assembly 120.

Figures 3, 4:
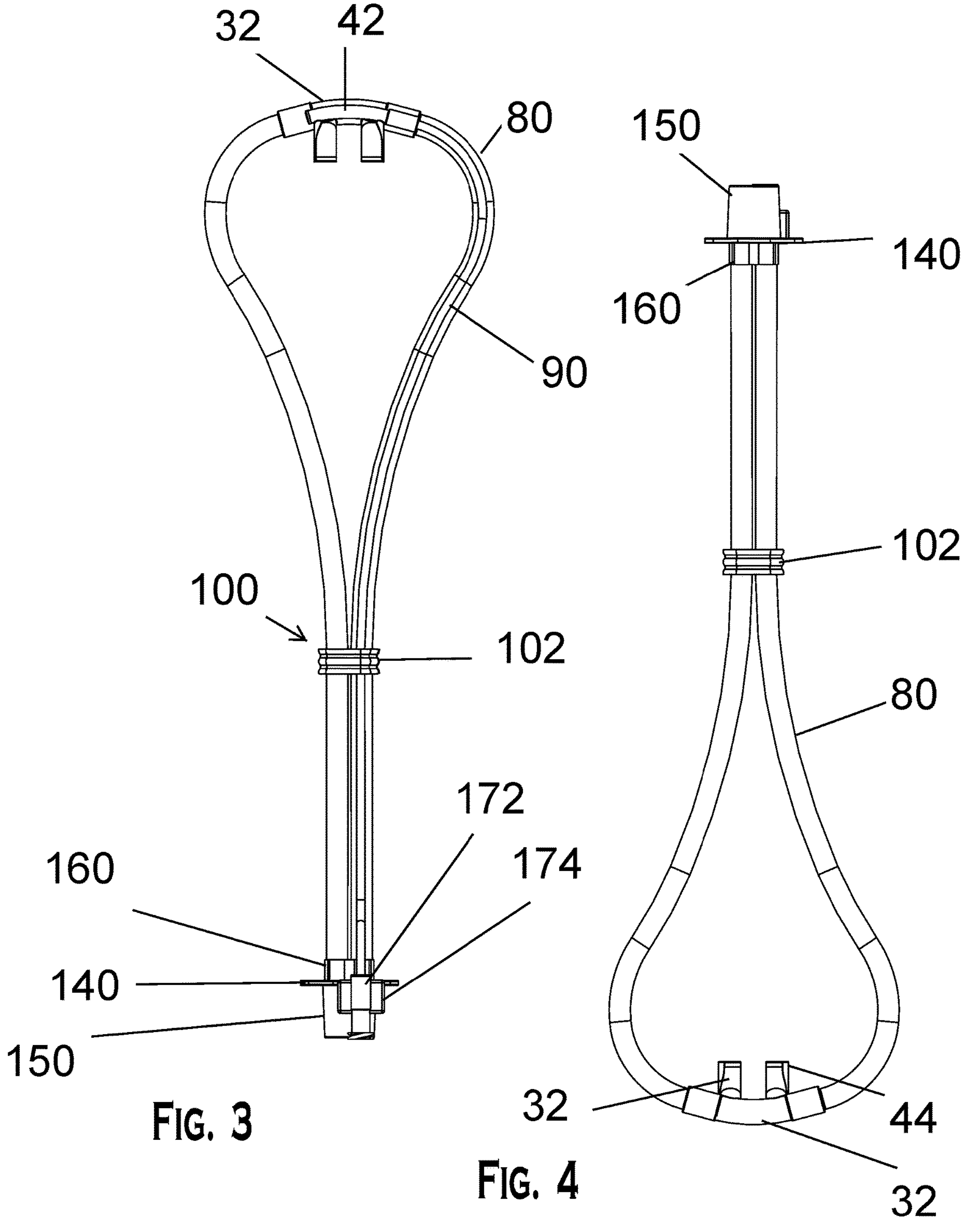
FIG. 3 is a top perspective view of the invention of FIG. 2.
FIG. 4 is a bottom perspective view of the invention of FIG. 3.
Figures 10, 11:
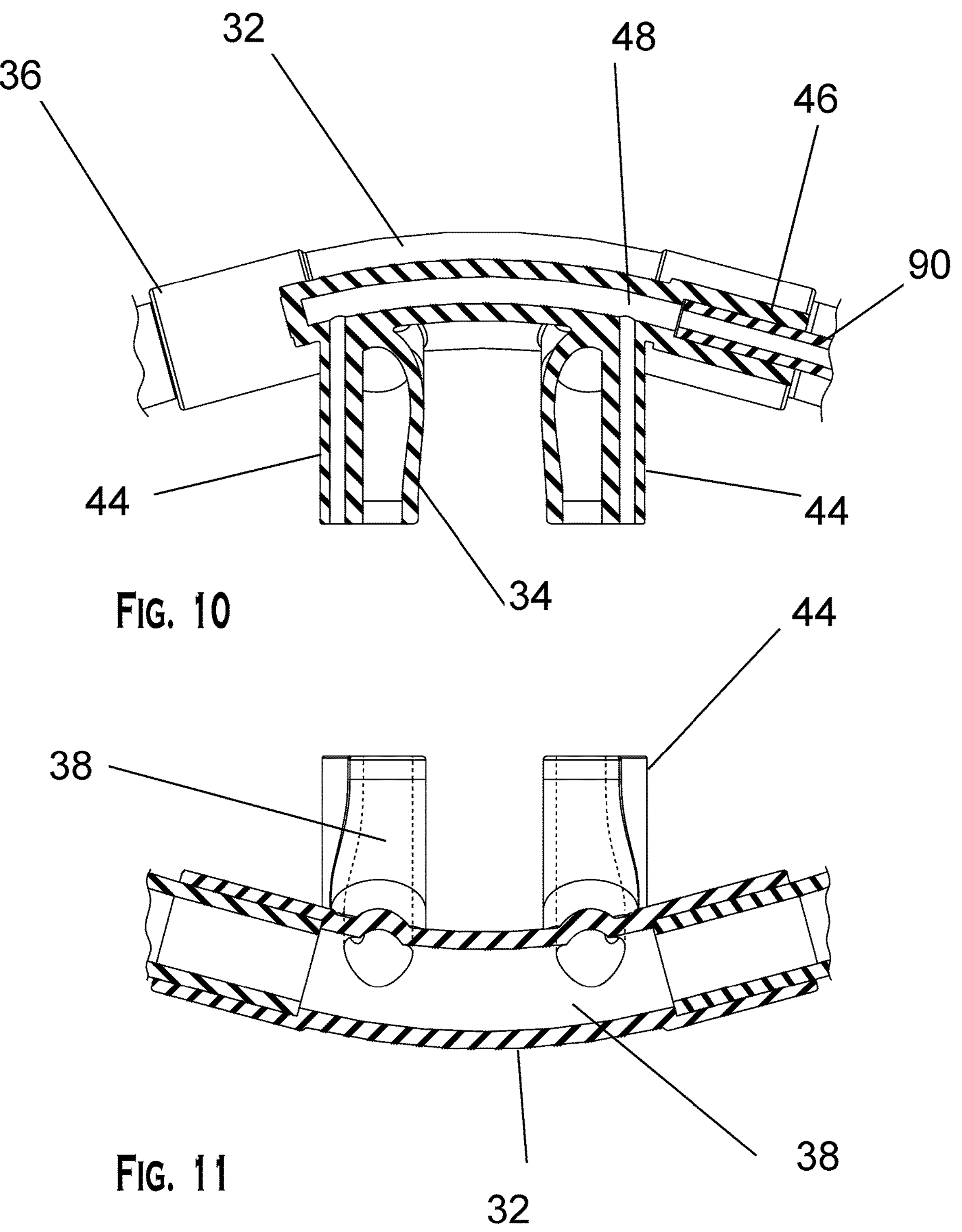
FIG. 10 is a top, enlarged cross-sectional view of one of the components of the invention of FIG. 9.
FIG. 11 is a bottom, enlarged cross-sectional view of one of the components of the invention of FIG. 10.
Figures 12, 13:
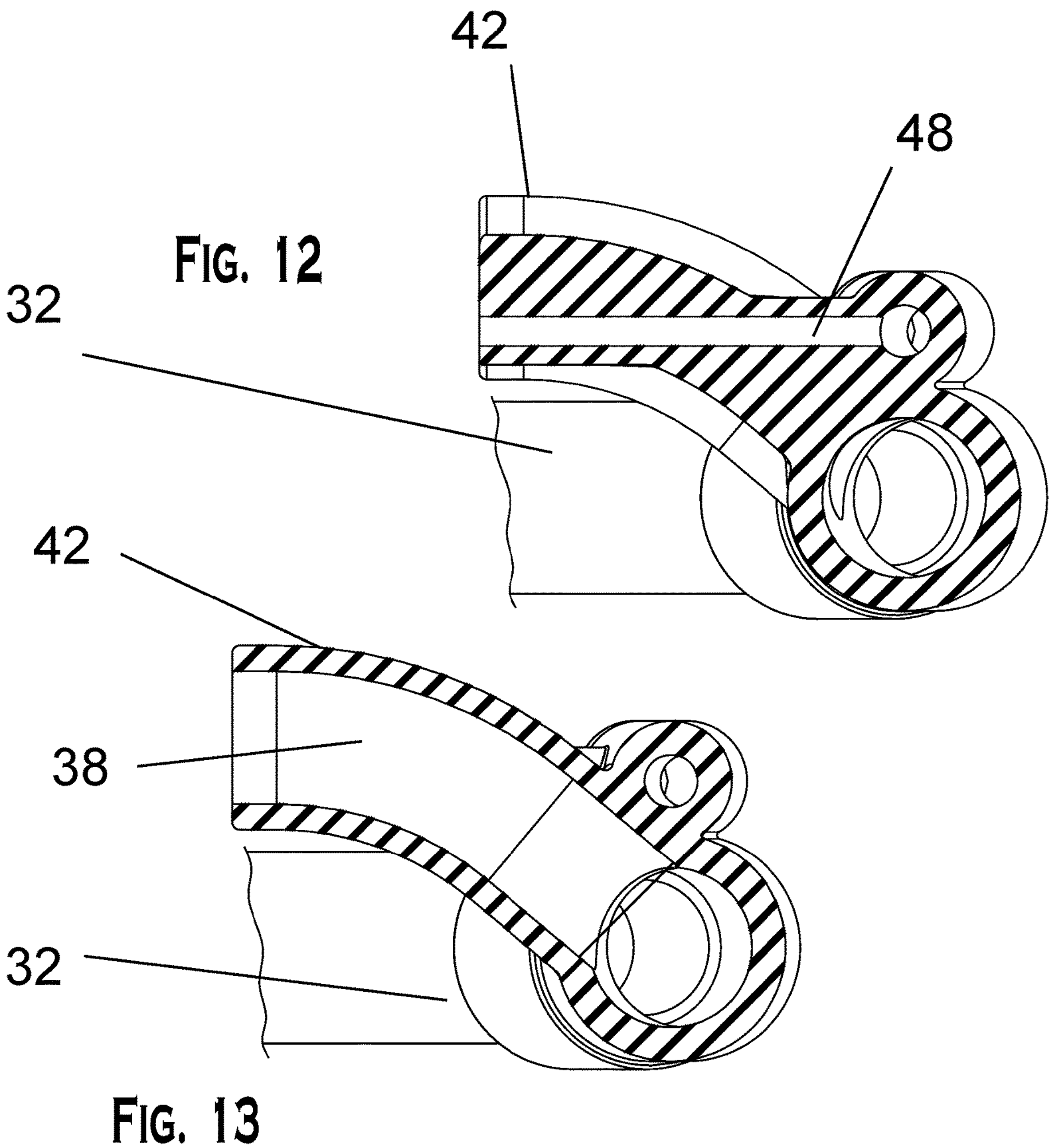
FIG. 12 is an enlarged cross-sectional view of one of the components of the invention of FIG. 11.
FIG. 13 is an enlarged cross-sectional view of one of the components of the invention of FIG. 12.

In the exemplary embodiment, the nasal cannula 20 generally includes an air flow nasal prong 30 and a medicinal flow nasal prong 40 as shown in FIG. 3. In the exemplary embodiment, the air flow nasal prong 30 is a hollow elongated cylindrical member 32. One of ordinary skill in the art would understand the applicant's design is not the exclusive embodiment. In the exemplary embodiment, the air flow nasal prong 30 further includes a set of dual nasal receivers 34. The set of dual nasal receivers 34 are curved tubular hollow members protruding from the central region of the hollow elongated cylindrical member 32. One of ordinary skill in the art would understand the applicant's design is not the exclusive embodiment. In the exemplary embodiment, the dual nasal receivers 34 further include an inner wall 34A and an outer wall 34B. In the exemplary embodiment, the air flow nasal prong 30 further includes an air tube receiver 36 on either side of the hollow elongated cylindrical member 32. One of ordinary skill in the art would understand the applicant's design is not the exclusive embodiment. In the exemplary embodiment, the air flow nasal prong 30 further includes an lower air passageway 38 along the inner region of the hollow elongated cylindrical member 32 and the inner wall 34A of the set of dual nasal receivers as shown in FIG. 11.

Figures 8, 9:
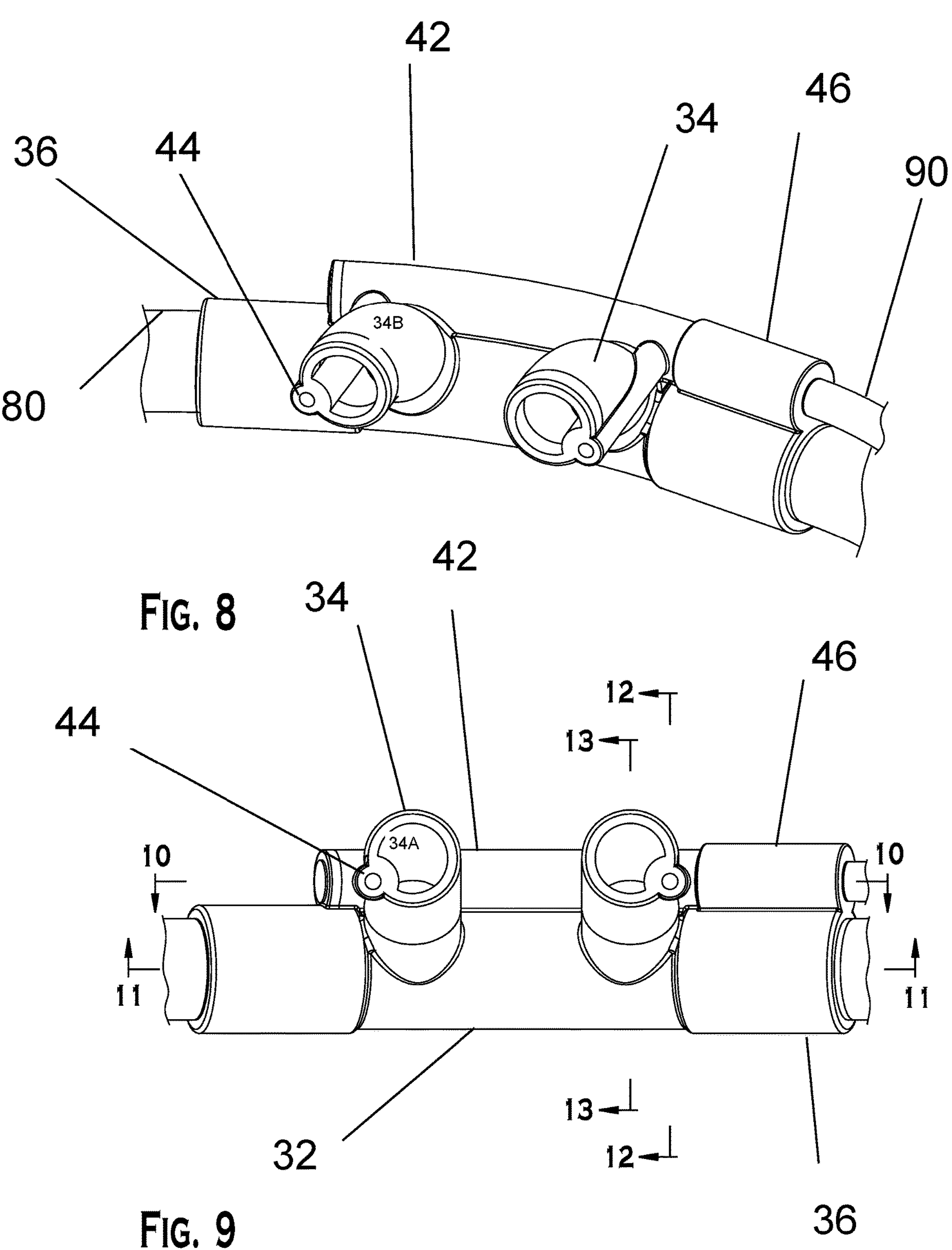
FIG. 8 is a top enlarged view of one of the components of the invention of FIG. 7.
FIG. 9 is a bottom enlarged view of one of the components of the invention of FIG. 8.

In the exemplary embodiment, the medicinal flow nasal prong 40 is generally constructed in accordance with the following main component: an elongated tube member 42 which is hollow and closed off at one end thereof as shown in FIG. 9. One of ordinary skill in the art would understand the applicant's design is not the exclusive embodiment. The elongated tube member 42 is positioned and fixed to the top of the hollow elongated cylindrical member 32 of the air flow nasal prong 30. In the exemplary embodiment, the medicinal flow nasal prong 40 further includes a dual set of medicinal distributors 44. The medicinal distributors 44 are hollow members that extend perpendicularly from the elongated tube member 42 and are integral with an outer wall 34B of the nasal receiver 34 in which the medicinal distributors 44 extend inwards on the inner wall 34A and outwards on the outer wall 34B as shown in FIGS. 8-9.

In the exemplary embodiment, the medicinal flow nasal prong 40 further includes a medicinal tube receiver 46. The medicinal tube receiver 46 is fixed to one end of the elongated tube member 42 and includes an opening for the insertion of a medicinal flow tube 90 as shown in FIG. 8. One of ordinary skill in the art would understand the applicant's design is not the exclusive embodiment. In the exemplary embodiment, the medicinal flow nasal prong 40 further includes a lower medicinal passageway 48 which extends along the inner portion of the elongated tube member 42 and connects both the elongated tube member 42 and the medicinal distributors 44 as shown in FIG. 10. One of ordinary skill in the art would understand the applicant's design is not the exclusive embodiment.

Figure 16:
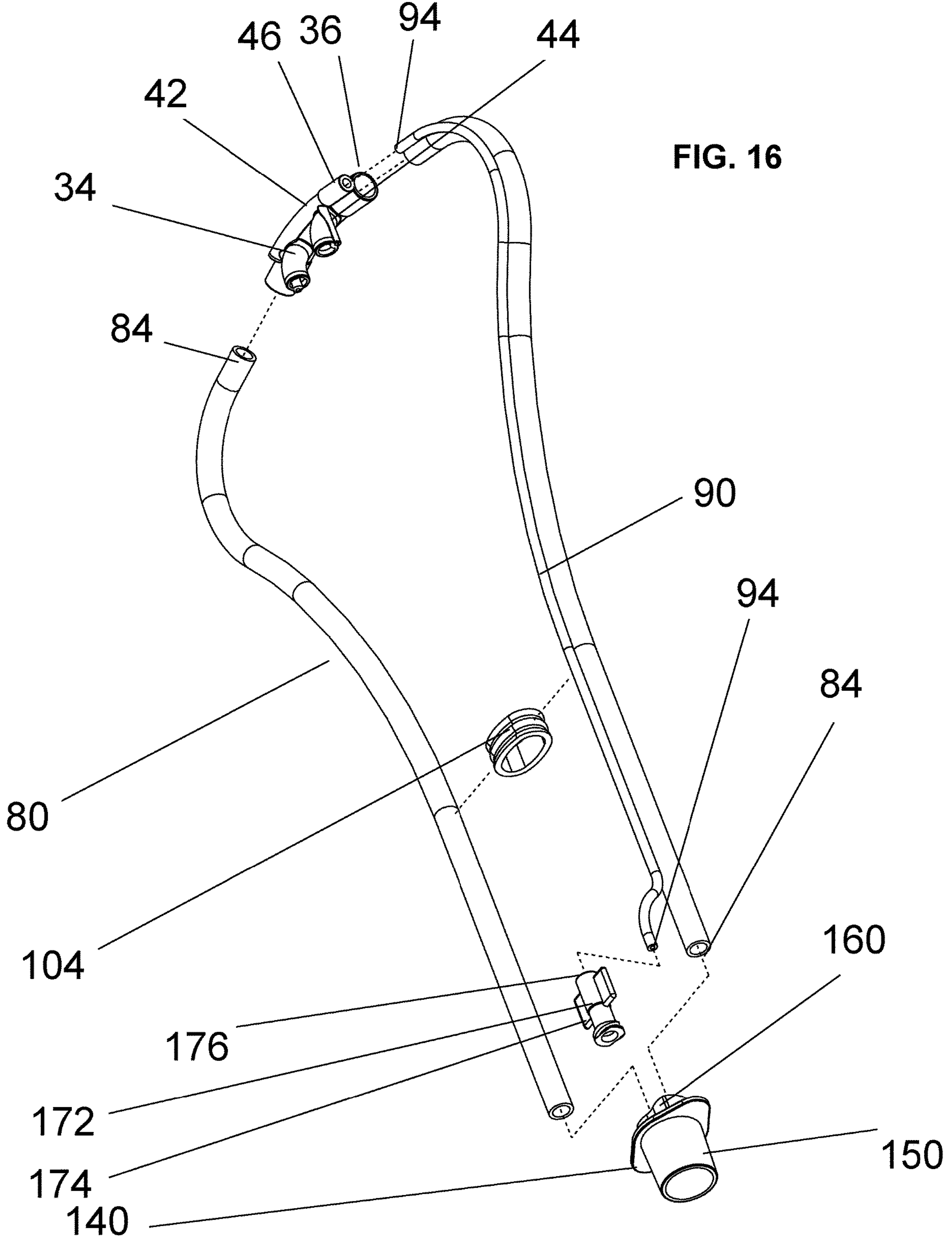
FIG. 16 is a rear, top, right-side exploded view of the invention of FIG. 15.

In the exemplary embodiment, the flow stream vessel 70 is generally constructed in accordance with the following main components: a set of air flow tubes 80, a medicinal flow tube 90 and an O-ring 100 as shown in FIG. 3. One of ordinary skill in the art would understand the applicant's design is not the exclusive embodiment. In the exemplary embodiment, the set of air flow tubes 80 are elongated tubular members 82 as shown in FIG. 16. One of ordinary skill in the art would understand the applicant's design is not the exclusive embodiment. In the exemplary embodiment, each of the air flow tubes 80 further include an air flow tube insert 84 located on each end thereof as shown in FIG. 16. The airflow tube insert is a grasping member. One of ordinary skill in the art would understand the applicant's design is not the exclusive embodiment. In the exemplary embodiment, the air flow tube 80 further includes an upper air passageway 86 extending and running along the length of the inner portion of each of the elongated tubular members 82. One of ordinary skill in the art would understand the applicant's design is not the exclusive embodiment.

Figures 5, 6, 7:
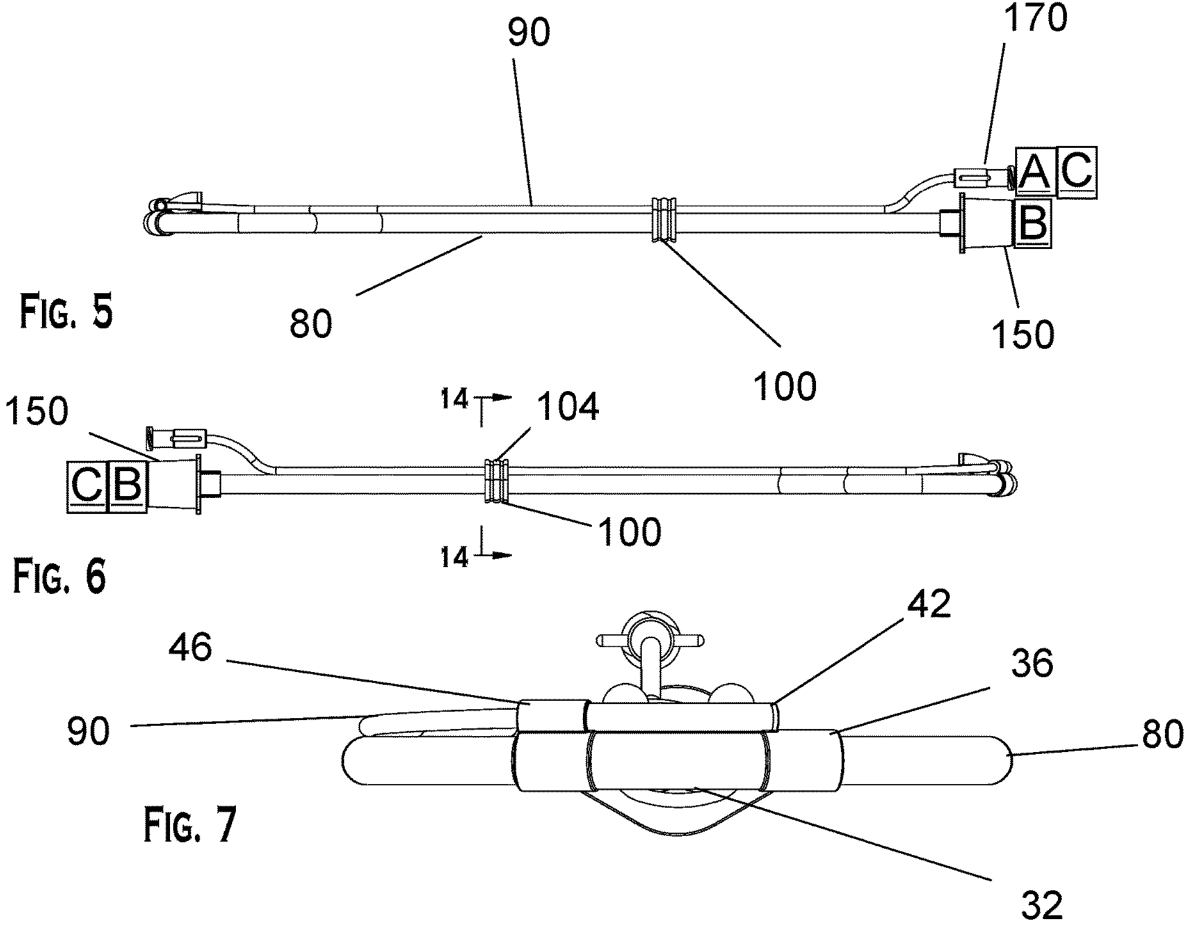
FIG. 5 is a left-side perspective view of the invention of FIG. 4.
FIG. 6 is a right-side perspective view of the invention of FIG. 5.
FIG. 7 is a front perspective view of the invention of FIG. 6.

In the exemplary embodiment, the medicinal flow tube 90 is an elongated tubular member 92 with an s-shaped bend at one end thereof as shown in FIG. 5. One of ordinary skill in the art would understand the applicant's design is not the exclusive embodiment. In the exemplary embodiment, the medicinal flow tube 90 further includes a medicinal flow tube insert 94 on each end of the elongated tubular member 92 for connecting to both the nasal cannula 20 and the mount assembly 120 as shown in FIG. 3. One of ordinary skill in the art would understand the applicant's design is not the exclusive embodiment. In the exemplary embodiment, the medicinal flow tube 90 further includes a upper medicinal passageway 96 extending the length and running along the inner portion of the elongated tubular member 92. One of ordinary skill in the art would understand the applicant's design is not the exclusive embodiment.

In the exemplary embodiment, the O-ring 100 is a circular member 102. One of ordinary skill in the art would understand the applicant's design is not the exclusive embodiment. In the exemplary embodiment, the O-ring 100 further includes a grip 104. The grip 104 is a plurality of indented and raised circular rings located on the outer rim of the circular member 102 as shown in FIG. 6. One of ordinary skill in the art would understand the applicant's design is not the exclusive embodiment. In the exemplary embodiment, the O-ring 100 further includes a through-hole 106. One of ordinary skill in the art would understand the applicant's design is not the exclusive embodiment.

Figures 14, 15:
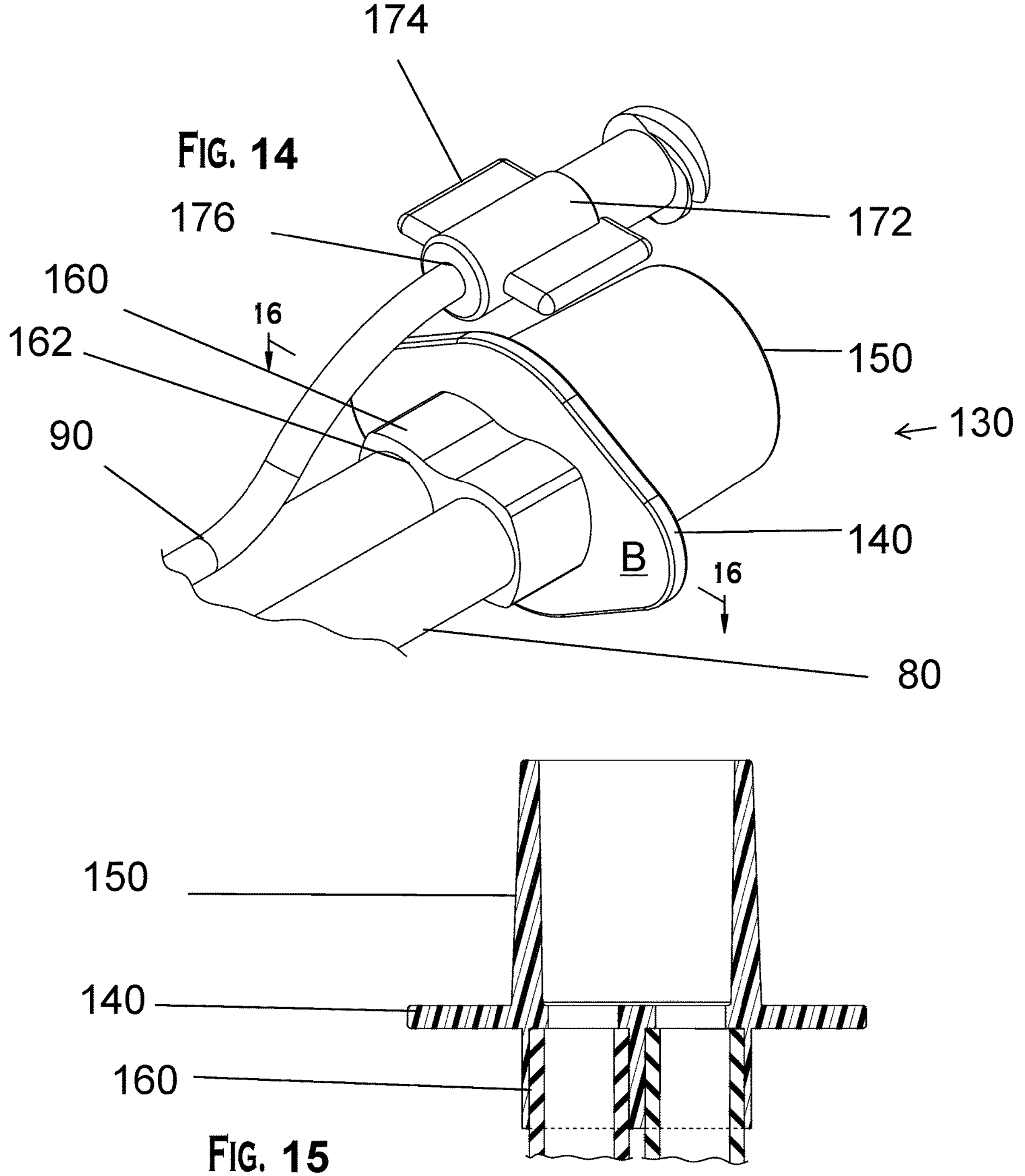
FIG. 14 is a front, left-side enlarged view of one of the components of the invention of FIG. 13.
FIG. 15 is a bottom, enlarged cross-sectional view of one of the components of the invention of FIG. 14.

In the exemplary embodiment, the mount assembly 120 is generally constructed in accordance with the following main components: an air passage device 130 and a luer lock connector 170 as shown in FIG. 14. One of ordinary skill in the art would understand the applicant's design is not the exclusive embodiment. In the exemplary embodiment, the air passage device 130 is generally constructed in accordance with the following main components: a gasket 140, a head piece 150 and a pair of extended receivers 160 as shown in FIG. 14. One of ordinary skill in the art would understand the applicant's design is not the exclusive embodiment. In the exemplary embodiment, the gasket 140 is a plate like structure. One of ordinary skill in the art would understand the applicants design is not the exclusive embodiment. In the exemplary embodiment, the gasket 140 further includes a pair of tube receiving passageways 142 located in the central region of the gasket 140 as shown in FIG. 14. One of ordinary skill in the art would understand the applicant's design is not the exclusive embodiment.

In the exemplary embodiment, the gasket 140 further includes a first face A and a second face B. One of ordinary skill in the art would understand the applicant's design is not the exclusive embodiment. In the exemplary embodiment, the head piece 150 is an elongated cylindrical component as shown in FIG. 14. One of ordinary skill in the art would understand the applicant's design is not the exclusive embodiment. In the exemplary embodiment, the pair of extended receivers 160 are an elongated member with a pair of insertion holes 162 as shown in FIG. 14. One of ordinary skill in the art would understand the applicant's design is not the exclusive embodiment.

In the exemplary embodiment, the luer lock connector 170 is generally constructed with an elongated cylindrical member 172 as shown in FIG. 14. One of ordinary skill in the art would understand the applicant's design is not the exclusive embodiment. In the exemplary embodiment, the luer lock connector 170 further includes a pair of flaps 174. In the exemplary embodiment, the flaps 174 are flat protrusions extending outward from the central region of the elongated cylindrical member 172 as shown in FIG. 14. One of ordinary skill in the art would understand the applicant's design is not the exclusive embodiment. In the exemplary embodiment, the luer lock connector 170 further includes a luer lock connector receiving passage 176 located at each end of the elongated cylindrical member 172. One of ordinary skill in the art would understand the applicant's design is not the exclusive embodiment.

In the exemplary embodiment, the medicinal diffuser system 1 is generally constructed in the following way. In the exemplary embodiment, the air flow tube insert 84 of the air flow tubes 80 are lined with an adhesive. The air flow tube insert 84 of each of the air flow tubes 80, are then inserted into the air tube receivers 36 of the air flow nasal prong 30 to create a seal tight fit. One of ordinary skill in the art would understand the applicant's design is not the exclusive embodiment. In the exemplary embodiment, the elongated tube member 42 of the medicinal flow nasal prong 40 is fixed to the top of the hollow elongated cylindrical member 32 of the air flow nasal prong 30 while the nasal receivers 34 are fixed to the central region of the hollow elongated cylindrical member 32 of the air flow nasal prong 30. One of ordinary skill in the art would understand the applicant's design is not the exclusive embodiment. In the exemplary embodiment, the medicinal distributors 44 are fixed to the central region of the elongated tube member 42 of the medicinal flow nasal prong 40. In the exemplary embodiment, the medicinal distributors 44 of the medicinal flow nasal prong 40 are fixed to the outer edge of each of the nasal receivers 34 of the air flow nasal prong 30. One of ordinary skill in the art would understand the applicant's design is not the exclusive embodiment. In the exemplary embodiment, the medicinal flow tube 90 is fixed to the top of one of the air flow tubes 80 depending on the design preference. One of ordinary skill in the art would understand the applicant's design is not the exclusive embodiment. In the exemplary embodiment, the medicinal flow tube insert 94 of the medicinal flow tube 90 is lined with an adhesive. One of ordinary skill in the art would understand the applicant's design is not the exclusive embodiment. In the exemplary embodiment, the medicinal flow tube insert 94 is fitted into the medicinal tube receiver 46 of the medicinal flow nasal prong 40 for a seal tight fit as shown in FIG. 16. One of ordinary skill in the art would understand the applicant's design is not the exclusive embodiment. In the exemplary embodiment, the plurality of tubes 80, 90 are threaded through the through-hole 106 of the O-ring 100 as shown in FIG. 3. One of ordinary skill in the art would understand the applicant's design is not the exclusive embodiment.

In the exemplary embodiment, the head piece 150 is fixed to the first face A of the gasket 140 as shown in FIG. 2. One of ordinary skill in the art would understand the applicant's design is not the exclusive embodiment. In the exemplary embodiment, the extended receivers 160 are fixed to the second face B of the gasket 140, over the pair of tube receiving passageways 142 as shown in FIG. 14. One of ordinary skill in the art would understand the applicant's design is not the exclusive embodiment. In the exemplary embodiment, the air flow tube inserts 84 are lined with an adhesive and the air flow tube inserts 84 are fitted into the extended receivers 160 for a seal tight fit. One of ordinary skill in the art would understand the applicant's design is not the exclusive embodiment.

In the exemplary embodiment, the medicinal flow tube insert 94 is lined with an adhesive in which the medicinal flow tube insert 94 is fitted into the luer lock connector receiving passage 176 of the luer lock connector 170 for a seal tight fit. One of ordinary skill in the art would understand the applicant's design is not the exclusive embodiment. In the exemplary embodiment, the head piece 150 of the mount assembly 120 is fitted to an air supply B.

In one embodiment, a propellant C is fitted to the air supply B in order to aid in the distribution of the gas. One of ordinary skill in the art would understand the applicant's design is not the exclusive embodiment.

In the exemplary embodiment, the luer lock connector receiving passage 176 of the luer lock connector 170 is inserted into a medicinal supply A. One of ordinary skill in the art would understand the applicant's design is not the exclusive embodiment.

In one embodiment, the luer lock connector 170 can be fastened to a such as aerosolized medicine device, such as a mesh nebulizer A and take the place of the medicinal supply A. One of ordinary skill in the art would understand the applicant's design is not the exclusive embodiment. For instance other nebulizers could be used including but not limited to pneumatic, mechanical or other electronic nebulizers.

The mesh nebulizer A would distribute a medicinal particle size of 1-5.5 μm. In another embodiment, the mesh nebulizer A would distribute a medicinal particle size of 0.5-4.5 μm. In another embodiment, the mesh nebulizer A would distribute on average a medicinal particle size of 3 μm. In another embodiment, the mesh nebulizer A would distribute on average a medicinal particle size of 2 μm.

In an exemplary embodiment, a propellant C is fitted to the mesh nebulizer A to aid in the distribution of the medicine through the mesh nebulizer A. The propellant C may be a compressed gas, such as air, oxygen, noble gas, or other known gas, to propel medicinal particles through the medicinal flow tube 90 to be inhaled by the patient. One of ordinary skill in the art would understand the applicant's design is not the exclusive embodiment.

In the exemplary embodiment, the medicinal diffuser system 1 allows for a caregiver to administer a medicinal agent to the patient while the patient continues to have a steady flow of oxygen. The air passage device 130 of the mount assembly 120 is connected to the air supply B while the luer lock connector 170 is fastened to the medicinal supply A.

The nasal cannula 20 is placed over a patient's head. The nasal receivers 34 and the medicinal distributors 44 are inserted into the nasal cavity of the patient. The air travels through upper air passageway 86 and along the air flow tubes 80, into the air flow nasal prong 30 where it is directed into lower air passageway 38 and flows through either of the nasal receivers 34 and maintains a steady flow. The medicinal agent travels through the upper medicinal passageway 96 and along the medicinal flow tube 90, and directed into the lower medicinal passageway 48 of medicinal flow nasal prong 40 where flows into either of the medicinal distributors 44. The patient is then able to have a steady flow of oxygen while the medicinal agent is distributed into the body via the nasal cavity.

The foregoing illustrates some of the possibilities for practicing the invention. Many other embodiments are possible within the scope and spirit of the invention. Therefore, more or less of the aforementioned components can be used to conform to that particular purpose. It is, therefore, intended that the foregoing description be regarded as illustrative rather than limiting, and that the scope of the invention is given by the appended claims together with their full range of equivalents.

What is claimed is:

1. A medicinal diffuser system comprising:

a nasal cannula having:

an air flow nasal prong with a set of nasal receivers; and a medicinal flow nasal prong having a set of medicinal distributors, each medicinal distributor is positioned integral to an outer wall of each nasal receiver of the set of nasal receivers, each medicinal distributor further extends away from the nasal receiver on an outer wall of the nasal receiver and extends into a passageway of the nasal receiver on an inner wall of each nasal receiver;

a flow stream vessel having:

a set of air flow tubes independently connected to air flow nasal prong; and a medicinal flow tube independently connected to the medicinal flow nasal prong;

and a mount assembly having:

an air passage device in communication with the set of air flow tubes and releasably connectable with an air supply; and a luer lock connector connected to the medicinal flow tube and releasably connectable to a medicinal supply to allow for a steady flow of medicine to be released independent of air supply; and wherein the set of medicinal distributors are coupled to an elongated tube member, the elongated tube member is closed at one end providing medicinal particles to flow into the elongated tube member through a medicinal tube receiver.

2. The medicinal diffuser system of claim 1, wherein the air in the air flow nasal prong is deflected into the nasal receivers.

3. The medicinal diffuser system of claim 2, wherein the medicine in the medicinal flow nasal prong is deflected into the medicinal distributors.

4. The medicinal diffuser system of claim 3, wherein the air flow nasal prong is a hollow elongated cylindrical member.

5. The medicinal diffuser system of claim 4, wherein the air flow nasal prong further includes an air tube receiver on either side of the elongated cylindrical member.

6. The medicinal diffuser system of claim 5, wherein the medicinal flow nasal prong further includes a medicinal tube receiver on one side of the elongated hollow member.

7. The medicinal diffuser system of claim 6, wherein the set of air flow tubes further includes a set of air flow tube inserts located on each open end thereof.

8. The medicinal diffuser system of claim 7, wherein the set of air flow tubes further includes an air passageway extending the length of the tubes.

9. The medicinal diffuser system of claim 8, wherein the medicinal flow tube further includes an insert at each end of the medicinal flow tube.

10. The medicinal diffuser system of claim 9, wherein the medicinal flow tube further includes a medicinal passageway extending the length of the medicinal flow tube.

11. The medicinal diffuser system of claim 10, wherein the set of air flow tubes and the medicinal flow tube is threaded through an O-ring.

12. The medicinal diffuser system of claim 11, wherein the air passage device further comprises a gasket, a head piece and a pair of extended receivers.

13. The medicinal diffuser system of claim 12, wherein the gasket includes a pair of receiving passageways.

14. The medicinal diffuser system of claim 13, wherein the gasket further includes a first face and a second face.

15. The medicinal diffuser system of claim 14, further includes the pair of extended receivers, each extended receiver is an elongated member with a plurality of insertion holes located over the receiving passageways of the gasket.

16. The medicinal diffuser system of claim 15, wherein the extended receivers are located over the receiving passageways of the gasket.

17. The medicinal diffuser system of claim 16, wherein the luer lock connector further includes a female receiving passage.

18. The medicinal diffuser system of claim 17, wherein a steady flow of air is released while the medicinal agent is administered.

* * * * *